(12) United States Patent
McGuire et al.

(10) Patent No.: US 8,968,505 B2
(45) Date of Patent: *Mar. 3, 2015

(54) LETTERPRESS APPLICATION OF ELASTOMERIC COMPOSITIONS

(71) Applicant: The Procter & Gamble Company, Cincinnati, OH (US)

(72) Inventors: Kenneth Stephen McGuire, Montgomery, OH (US); Mary Lee Amirpour, West Chester, OH (US); Urmish Popatlal Dalal, Milford, OH (US); Fred Naval Desai, Fairfield, OH (US); Charles Bruce Lambert, Mason, OH (US); David Richard Tucker, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/925,925
(22) Filed: Jun. 25, 2013
(65) Prior Publication Data
 US 2013/0287953 A1   Oct. 31, 2013
 Related U.S. Application Data

(60) Continuation of application No. 12/644,065, filed on Dec. 22, 2009, now Pat. No. 8,496,776, which is a division of application No. 11/087,345, filed on Mar. 23, 2005, now Pat. No. 7,658,811.

(60) Provisional application No. 60/557,272, filed on Mar. 29, 2004.

(51) Int. Cl.
 *B32B 5/04* (2006.01)
 *B29C 55/04* (2006.01)
 (Continued)

(52) U.S. Cl.
 CPC ............ *B05D 1/28* (2013.01); *A61F 13/15593* (2013.01); *A61F 2013/15373* (2013.01);
 (Continued)

(58) Field of Classification Search
 CPC .................... A61F 13/15593; A61F 13/15601; A61F 13/15609; A61F 13/49009; A61F 13/4902; A61F 2013/15373; B05C 1/08; B05C 1/0834; B05C 1/0856; B05C 1/16; B05C 9/14; B05D 1/28; B29C 55/04; B29C 55/08; B29C 55/18; B32B 5/04; B32B 2038/0028; B41M 1/02; B41M 1/04; B41M 1/10; B41M 1/26; B41M 3/006
 USPC .................. 156/176, 229, 230, 277; 427/276, 427/428.06, 428.15, 428.19; 118/212; 604/385.24
 See application file for complete search history.

(56) References Cited

U.S. PATENT DOCUMENTS 4,322,467 A   3/1982  Heimbach et al.
4,329,309 A   5/1982  Kelly
(Continued)

FOREIGN PATENT DOCUMENTS

DE  19516037 A1  11/1996
EP  0 472 942 B1   9/1995
(Continued)

OTHER PUBLICATIONS

ISR and WO, PCT/US2005/009994, date of mailing Sep. 22, 2005.
(Continued)

*Primary Examiner* — Michael Tolin
(74) *Attorney, Agent, or Firm* — Christian M. Best; Charles R. Ware

(57) ABSTRACT

A process of manufacturing a stretch composite is disclosed. The process comprises providing a polyolefin based substrate, providing a letterpress adhesive application system comprising a pattern roll and an applicator roll, and depositing a molten, non-adhesive, elastomeric composition onto the applicator roll. The process further comprises transferring only a portion of the elastomeric composition that is on the applicator roll, from the applicator roll to the pattern roll, by contacting the pattern roll with the elastomeric composition that is on the applicator roll, and transferring substantially all of the elastomeric composition from the pattern roll to the substrate, by contacting the substrate with the elastomeric composition that is on the pattern roll, without damaging the substrate.

26 Claims, 4 Drawing Sheets

(51) Int. Cl.
  *B29C 55/08* (2006.01)
  *B05D 1/28* (2006.01)
  *A61F 13/15* (2006.01)
  *B41M 3/00* (2006.01)
  *A61F 13/49* (2006.01)
  *B29C 55/18* (2006.01)
  *B41M 1/02* (2006.01)
  *B41M 1/26* (2006.01)
  *B32B 38/00* (2006.01)

(52) U.S. Cl.
  CPC . *B29C55/04* (2013.01); *B32B 5/04* (2013.01); *B32B 2038/0028* (2013.01); *B41M 3/006* (2013.01); *A61F 13/4902* (2013.01); *B29C 55/08* (2013.01); *B29C 55/18* (2013.01); *B32B 38/0012* (2013.01); *B41M 1/02* (2013.01); *B41M 1/26* (2013.01)
  USPC ...... 156/229; 156/230; 156/277; 427/428.15; 604/385.24

(56) References Cited

U.S. PATENT DOCUMENTS

| | | | |
|---|---|---|---|
| 4,686,172 A | 8/1987 | Worns et al. | |
| 4,705,584 A | 11/1987 | Lauchenauer | |
| 4,761,341 A | 8/1988 | Rosiak et al. | |
| 4,895,568 A * | 1/1990 | Enloe | 604/385.27 |
| 5,055,103 A | 10/1991 | Nomura et al. | |
| 5,217,798 A | 6/1993 | Brady et al. | |
| 5,300,057 A | 4/1994 | Miller et al. | |
| 5,468,237 A | 11/1995 | Miller et al. | |
| H1517 H | 2/1996 | Erickson et al. | |
| 5,547,736 A | 8/1996 | Simon et al. | |
| 5,662,758 A | 9/1997 | Hamilton et al. | |
| 5,671,678 A | 9/1997 | Bolte et al. | |
| 5,871,607 A | 2/1999 | Hamilton et al. | |
| 5,910,224 A | 6/1999 | Morman | |
| 6,060,009 A | 5/2000 | Welygan et al. | |
| 6,193,701 B1 | 2/2001 | Van Gompel et al. | |
| 6,193,918 B1 | 2/2001 | McGuire et al. | |
| 6,245,050 B1 | 6/2001 | Odorzynski et al. | |
| 6,465,073 B1 | 10/2002 | Morman et al. | |
| 6,476,289 B1 | 11/2002 | Buell et al. | |
| 6,495,229 B1 | 12/2002 | Carte et al. | |
| 6,531,025 B1 | 3/2003 | Lender et al. | |
| 6,531,027 B1 | 3/2003 | Lender et al. | |
| 6,682,514 B1 | 1/2004 | Brunner | |
| 6,827,806 B2 | 12/2004 | Uitenbroek et al. | |
| 6,833,179 B2 | 12/2004 | May et al. | |
| 6,875,710 B2 | 4/2005 | Eaton et al. | |
| 7,658,811 B2 * | 2/2010 | McGuire et al. | 156/230 |
| 8,496,776 B2 * | 7/2013 | McGuire et al. | 156/230 |
| 2002/0007164 A1 | 1/2002 | Boggs et al. | |
| 2002/0180097 A1 | 12/2002 | Giachetto et al. | |
| 2003/0084996 A1 | 5/2003 | Alberg et al. | |
| 2003/0087059 A1 | 5/2003 | Jackson et al. | |
| 2003/0087098 A1 | 5/2003 | Eaton et al. | |
| 2003/0088220 A1 | 5/2003 | Molander et al. | |
| 2003/0088228 A1 | 5/2003 | Desai et al. | |
| 2003/0091807 A1 | 5/2003 | Desai et al. | |
| 2004/0044323 A1 | 3/2004 | Roessler et al. | |
| 2004/0127881 A1 | 7/2004 | Stevens et al. | |
| 2004/0134596 A1 | 7/2004 | Rosati et al. | |
| 2004/0142110 A1 | 7/2004 | Branca et al. | |
| 2004/0178544 A1 * | 9/2004 | Jackson et al. | 264/556 |

FOREIGN PATENT DOCUMENTS

| | | |
|---|---|---|
| EP | 0 745 433 B1 | 12/1996 |
| EP | 1 081 672 A2 | 3/2001 |
| JP | 07 089012 | 4/1995 |
| JP | 1053963 | 2/1998 |
| WO | WO 94/01507 A1 | 1/1994 |
| WO | WO 96/24485 A1 | 8/1996 |

OTHER PUBLICATIONS

All Office Actions, U.S. Appl. No. 12/644,065.
All Office Actions, U.S. Appl. No. 11/087,345.

* cited by examiner

LETTERPRESS APPLICATION OF ELASTOMERIC COMPOSITIONS

CROSS REFERENCE TO RELATED APPLICATIONS

This application is a continuation of U.S. patent application Ser. No. 12/644,065, filed on Dec. 22, 2009, now U.S. Pat. No. 8,496,776, granted on Jul. 30, 2013,which is a divisional of U.S. patent application Ser. No. 11/087,345, filed on Mar. 23, 2005, now U.S. Pat. No. 7,658,811, granted on Feb. 9, 2010, which claims the benefit of U.S. Provisional Patent Application Ser. No. 60/557,272, filed on Mar. 29, 2004. Priority is claimed to all of the above-listed patent applications. The entire disclosures of all of the above-listed patent applications are hereby incorporated by reference herein.

FIELD

The disclosure generally relates to a process of forming a stretch composite via transfer of elastomeric compositions onto a substrate via letterpress application. In this process, an elastomeric composition is substantially removed from raised surface elements of a pattern roll, i.e., the residual elastomer is less than 10%. In certain embodiments, the composite is subsequently incrementally stretched to at least partially break up the structure of the substrate in order to reduce its resistance to stretch. The stretch composites are useful for disposable articles, such as disposable absorbent articles including diapers, pull-on diapers, training pants, incontinence briefs, catamenial garments, baby bibs, and the like, and other disposable and durable articles, particularly garments including surgical garments and drapes, sportswear, outerwear and the like.

BACKGROUND

Disposable absorbent products (e.g., disposable diapers) typically include stretchable materials, such as elastic strands, in the waist region and the cuff regions to provide a snug fit and a good seal to a wearer's body. Pant-type absorbent articles further include stretchable materials in the side portions for easy application and removal of the article and for sustained fit of the article. Stretchable materials have also been used in the ear portions of taped diapers for adjustable fit of the article. Useful stretchable materials include elastomeric films, nonwovens, strands of natural or synthetic rubber, elastic scrim, and the like. Typically, these stretch regions are made separately and attached to the diaper using adhesives. In most cases, these designs deliver uniform and unidirectional stretch. Similarly, garments, both disposable and durable, also use elastic elements for improved fit and comfort.

An alternate approach that is capable of delivering multidirectional, non-uniform stretch has been disclosed in copending U.S. patent application Ser. Nos. 10/288,095, 10/288,126 and 10/429,433. This approach involves hot melt printing of one or more thermoplastic elastomers onto a substrate, followed by incremental stretching of the elasticized substrate that then confers the stretch properties of the elastomer to the substrate in a somewhat magnified form. Suitable printing processes disclosed therein include direct gravure, offset gravure, and flexographic printing. Each of these printing methods allows deposition of a predetermined amount of an elastomer in any shape and direction, thus giving a wide variety of design flexibility which ultimately results in improved fit of the overall diaper product. However, improvements are still needed.

Desirably, transfer of such an elastomeric composition from the means used to apply the elastomer to a substrate is substantially complete. Otherwise, the elastomeric composition can oxidize with resulting color degradation, or suffer degradation of other properties. Such degradation, as may result from incomplete transfer is more likely if the application means is heated.

Without being limited by theory, it is therefore important to understand the mechanism of transfer of an elastomer from an application means to a substrate. During this transfer, three forces are relevant. These forces include: i) the adhesive force between the surface of the application means and the elastomer; ii) the cohesive strength of the elastomer (i.e., the resistance of a single portion of an elastomeric composition to separation into two smaller portions); and iii) the adhesive force between the elastomer and the substrate and/or the strength of the substrate. In order to successfully transfer an elastomer to a substrate either one or both of the cohesive strength of the elastomer or the adhesive force between the elastomer and the surface of the application means must be less than the adhesive force between the elastomer and the substrate and/or the strength of the substrate. Typically, this problem has been solved by the use of heated printing processes where the cohesive strength of the heated elastomer is at a sufficiently low value because the elastomer has been maintained in a liquid or semi-liquid state. Thus, transfer of an elastomeric composition from an application means to a substrate typically is achieved through cohesive failure of the elastomer at the point of transfer from the application means to the substrate and a portion of the elastomer remains on the surface of the application means. The above conditions generally apply during, for example, gravure printing of elastomeric adhesives, where the viscosity is relatively low and the adhesive has strong affinity for the walls of the gravure elements and also the substrate. Importantly, cohesive failure means that there is a residual portion of adhesive on the application means that is not transferred.

On the other hand, elastomeric compositions that have good elasticity generally have a higher viscosity at a given temperature than a typical elastomeric adhesive. For reference, typical thermoplastic elastomers used in diapers have viscosities in excess of 1000 Pa·S at 175° C. Increased viscosity translates into a higher cohesive force of the elastomer and a need to heat to a higher application temperature to insure cohesive failure. Such a dynamic poses a problem for conventional direct gravure printing of high viscosity materials, since a point is reached when the cohesive strength of the elastomer either exceeds its adhesive strength with the substrate or it exceeds the strength of the substrate. Such conditions, in turn, result in either a failure of the elastomer to bond to the substrate or damage to the substrate. On the other hand, if temperature is increased to lower cohesive strength, the application temperature of the elastomeric composition may exceed the melting point of the substrate with resulting substrate damage or thermal degradation of the elastomer. Thus, there is a need for an application process that is capable of depositing high viscosity elastomeric compositions on substrates, without damaging these substrates.

SUMMARY

In one form, the present disclosure generally relates, in part, to a process of manufacturing a stretch composite. The process may comprise providing a polyolefin based substrate, providing a letterpress adhesive application system comprising a pattern roll and an applicator roll, and depositing a molten, non-adhesive, elastomeric composition onto the applicator roll. The process may further comprise transferring only a portion of the elastomeric composition that is on the applicator roll, from the applicator roll to the pattern roll, by contacting the pattern roll with the elastomeric composition that is on the applicator roll, and transferring substantially all of the elastomeric composition from the pattern roll to the substrate, by contacting the substrate with the elastomeric composition that is on the pattern roll, without damaging the substrate.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings, in which:

DETAILED DESCRIPTION

Definitions

Figure 1:
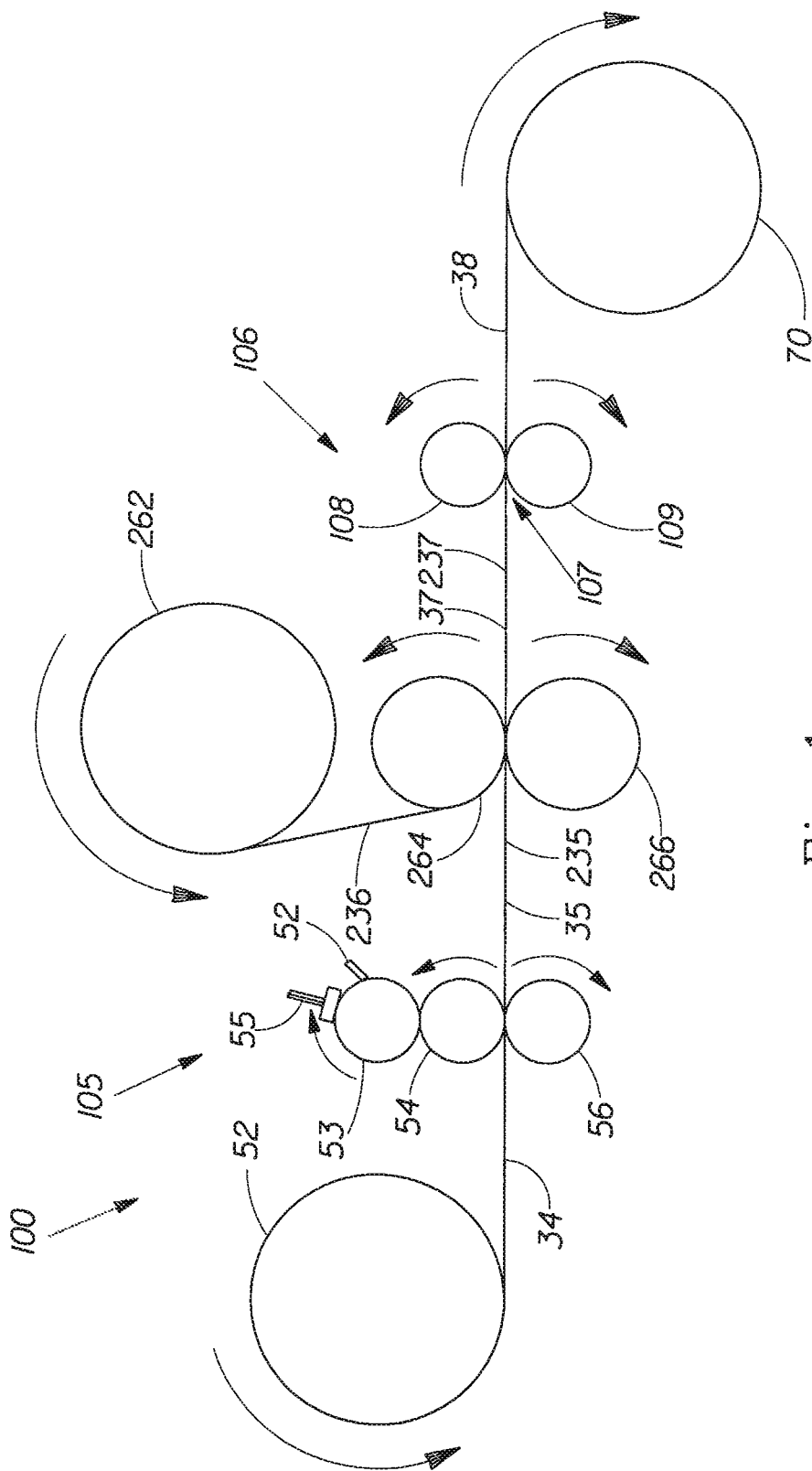
FIG. 1 is a schematic view of an apparatus for carrying out one embodiment of the process of the present invention.

The term "disposable" as used herein refers to products which generally are not intended to be laundered or otherwise restored or extensively reused in their original function, i.e., preferably they are intended to be discarded after about 10 or fewer uses, or more preferably after about 5 or fewer uses, or even more preferably after about a single use. It is preferred that such disposable articles be recycled, composted or otherwise disposed of in an environmentally compatible manner.

The term "disposable absorbent article" as used herein refers to a device that normally absorbs and retains fluids. In certain instances, the phrase refers to devices that are placed against or in proximity to the body of the wearer to absorb and contain the excreta and/or exudates discharged from the body, and includes such personal care articles as fastened diapers, pull-on diapers, training pants, swim diapers, adult incontinence articles, feminine hygiene articles, and the like. In other instances, the term also refers to protective or hygiene articles, for example, bibs, wipes, bandages, wraps, wound dressings, surgical drapes, and the like.

The term "adhesive" refers to materials that, when evaluated according to the peel test described in the TEST METHODS section below have a peel force greater than 3 N/cm.

The term "substrate" as used herein refers to a material that includes either a natural or synthetic material or any combination thereof, for example, nonwoven webs, woven webs, knitted fabrics, films, film laminates, nonwoven laminates, sponges, foams, and any combinations thereof.

The term "fibrous substrate" as used herein refers to a material comprised of a multiplicity of fibers that could be either a natural or synthetic material or any combination thereof, for example, nonwoven webs, woven webs, knitted fabrics, and any combinations thereof.

The term "nonwoven" as used herein refers to a material made from continuous and/or discontinuous fibers, without weaving or knitting, by processes such as airlaying, wet laying, spun-bonding, carding and melt-blowing. A nonwoven web can comprise one or more nonwoven layers, wherein each layer can include continuous and/or discontinuous fibers. Nonwoven webs can also comprise bicomponent fibers, which can have shell/core, side-by-side, or other known fiber structures.

The term "elastic" or "elastomeric" as used herein refers to any material that upon application of a biasing force, can stretch to an elongated length of at least about 160 percent of its relaxed, original length, without rupture or breakage, and upon release of the applied force, recovers at least about 55% of its elongation, preferably recovers substantially to its original length that is, the recovered length being less than about 120 percent, preferably less than about 110 percent, more preferably less than about 105 percent of the relaxed original length.

The term "inelastic" refers herein to any material that does not fall within the definition of "elastic" above.

The term "elastomer" as used herein refers to a polymer exhibiting elastic properties.

The term "extensible" or "inelastically elongatable" refers herein to any material that upon application of a biasing force to stretch beyond about 110 percent of its relaxed original length will exhibit permanent deformation, including elongation, rupture, breakage, and other defects in its structure, and/or changes in its tensile properties.

The term "letterpress" or "letterpress application system" refers herein to application means where a material is transferred to a substrate from an apparatus comprising a predetermined pattern of raised surface elements on a metallic roll surface where the shape of the individual elements defines the shape of the transferred material.

The term "necked material" refers to any material that has been narrowed in one direction by the application of a tensioning force.

The terms "machine direction" or "MD" as used herein refer to the direction of material flow through a process. The terms "cross machine direction" or "CD" refer to a direction perpendicular to the machine direction.

Substrate

Substrates (i.e., a first substrate or any additional substrate layers) suitable for use in the presently claimed processes have opposed first and second surfaces and may be selected from the group consisting of tissue, films, knitted fabric, woven fibrous webs, nonwoven fibrous webs (including air laid, wet laid, carded, meltblown and spunbonded webs), or combinations thereof. In some embodiments, the substrate is an extensible nonwoven web that comprises polyolefin fibers and/or filaments, such as polyethylene, polypropylene, etc. The substrate can also be a nonwoven-film laminate, which for example, may be used as the outer cover of a disposable diaper, training pant, adult incontinence product, etc. Ideally, the substrate has a thickness between about 0.05 mm and about 2 mm, preferably from about 0.1 mm to about 1 mm, and most preferably, from about 0.1 mm to about 0.5 mm.

Elastomeric Composition

The elastomeric composition of the present invention is characterized as having a peel force of less than about 3 N/cm, more preferably, less than about 2 N/cm, even more preferably, less than about 1 N/cm, and most preferably, less than about 0.8 N/cm. (The methodology used to determine the peel force of these elastomeric compositions is discussed in the TEST METHODS section below). As is discussed below, such relatively low peel force is believed necessary in order to achieve substantially complete transfer onto a substrate from a pattern roll.

Suitable elastomeric compositions comprise thermoplastic elastomers selected from the group consisting of styrenic block copolymers having a soft block comprising an olefin (preferred olefins include isoprene, butadiene, ethylene, propylene, butylene, and isobutylene), metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Such multi-block copolymers include both linear multi-block copolymers and branched copolymers where a plurality of blocks radiate out from a central block, commonly known as star polymers. Exemplary styrenic block copolymers include styrene-butadiene-styrene, styrene-isoprene-styrene, styrene-ethylene/butylene-styrene, styrene-ethylene/propylene-styrene, and the like. Commercially available styrenic block copolymers include KRATON® from the Shell Chemical Company of Houston, Tex.; SEPTON® from Kuraray America, Inc. of New York, N.Y.; and VECTOR® from Dexco Chemical Company of Houston, Tex. Commercially available metallocene-catalyzed polyolefins include EXX-POL® and EXACT® from Exxon Chemical Company of Baytown, Tex.; AFFINITY® and ENGAGE® from Dow Chemical Company of Midland, Mich. Commercially available polyurethanes include ESTANE® from Noveon, Inc., Cleveland, Ohio. Commercial available polyether amides include PEBAX® from Atofina Chemicals of Philadelphia, Pa. Commercially available polyesters include HYTREL® from E. I. DuPont de Nemours Co., of Wilmington, Del.

The elastomeric compositions may further comprise processing aids and/or processing oils to adjust the melt viscosity of the compositions. They include the conventional processing oil, such as mineral oil, as well as other petroleum-derived oils and waxes, such as paraffinic oil, naphthenic oil, petrolatum, microcrystalline wax, paraffin or isoparaffin wax. Synthetic waxes, such as Fischer-Tropsch wax; natural waxes, such as spermaceti, carnauba, ozokerite, beeswax, candelilla, ceresin, esparto, ouricuri, rezowax, and other known mined and mineral waxes are also suitable for use herein. Olefinic or diene oligomers and low molecular weight resins may also be used herein. The oligomers may be polypropylenes, polybutylenes, hydrogenated isoprenes, hydrogenated butadienes, or the like, with a weight average molecular weight between about 350 and about 8000.

In one embodiment, a phase change solvent is used as the processing aid. It can be incorporated into the elastomeric composition to lower the melt viscosity, rendering the composition processable at a temperature of 175° C. or lower, without substantially compromising the elastic and mechanical properties of the composition. Typically, the phase change solvent exhibits a phase change at temperatures ranging from about 40° C. to about 250° C. Detailed disclosure of the phase change solvents can be found in U.S. patent application Ser. No. 10/429,432, filed on Jul. 2, 2003. In some embodiments, the weight ratio of thermoplastic elastomer to processing oil or processing aid (e.g., a phase change solvent) in the elastomeric composition typically ranges from about 10:1 to about 1:2, preferably from about 5:1 to about 1:1, and more preferably about 2:1 to about 1:1.

In addition the elastomeric composition can comprise stabilizers and the like. For example, stabilizers can include both antioxidants and light stabilizers. Suitable antioxidants include sterically hindered phenolics. A commercially available antioxidant suitable for use in the elastomeric compositions of the present invention is IRGANOX 1010 available from Ciba Specialty Chemicals North America of Tarrytown, N.Y. Suitable light stabilizers include hindered amine light stabilizers. A commercially available ultraviolet light stabilizer is TINUVIN 123 also available from Ciba Specialty Chemicals North America.

The elastomeric compositions suitable for use with the present invention are also substantially tackifier free in order to help insure that adhesive failure at the pattern roll surface can be reliably achieved. As used herein the term "substantially tackifier free" is intended to mean that the elastomeric composition has less than about 5% by weight of a material commonly recognized in the adhesive arts as a tackifier. As is well known, tackifiers are added to adhesive formulations in order to increase the adhesion thereof. Materials having commercial utility as tackifiers include: rosin resins, cumarone-indene resins, terpene resins and hydrocarbon resins. Example 1 compares the release properties of suitable elastomeric compositions with prior art elastomeric adhesives.

Alternatively, the elastomeric composition may also comprise low molecular weight elastomers and/or elastomeric precursors of the above thermoplastic elastomers, and optional crosslinkers, or combinations thereof. For example, the thermoplastic elastomers described in copending U.S. patent application Ser. No. 10/610,605, filed in the name of Ashraf, et al. on Jul. 1, 2003 that comprise an elastomeric block copolymer having least one hard block and at least one soft block, a macro photoinitiator, a processing oil, and optionally, a thermoplastic polymer and/or a crosslinking agent contain such an elastomeric precursor. The weight average molecular weight of the low molecular weight elastomers or elastomeric precursors is between about 45,000 and about 150,000. In some embodiments, the weight ratio between thermoplastic elastomer to low molecular weight elastomers or elastomeric precursors to the thermoplastic elastomers in the composition typically ranges from about 10:1 to about 1:2, preferably from about 5:1 to about 1:1, and more preferably about 2:1 to about 1:1.

Suitable elastomeric compositions for use herein form elastomeric members that are elastic without further treatment and these elastomeric compositions do not include any volatile solvents with boiling point below 150° C. After the elastomeric composition has been applied to the substrate, however, post-treatments may be used to improve or enhance the elasticity and other properties including strength, modulus, and the like of the resulting elastomeric members. Typically, post-treatments converting the elastomeric compositions into elastomeric members by methods such as cooling, crosslinking, curing (e.g., via chemical, thermal or radiation means), pressing between nip rolls, and combinations thereof.

Letterpress Application

The present invention also requires the use of a letterpress application system which comprises either a pattern roll, a backing roll and an applicator roll. Such a letterpress application system differs from similar flexographic systems in the structure of the pattern roll. In the letterpress system described herein, the pattern roll has a substantially metallic structure. Such metallic structure is believed to be necessary for the required heat transfer to provide the cooling of the elastomeric composition discussed herein.

The external surface of the pattern roll comprises a predetermined pattern of raised surface elements. The individual elements can be rectilinear, curvilinear, or of any arbitrary shape. For example a regular shape such as circular or rectangular or an irregular shape. Adjacent elements can either have a gap between them or can be connected to form a continuous pattern.

The individual elements can be parallel or non-parallel to one another. Several elements can be put together to form a component of a finished article (e.g., a disposable diaper).

The raised elements can either be continuous or discontinuous along the surface of the roll. An example of a continuous pattern is a crosshatch pattern, having MD and CD stripes that run along the entire surface of the pattern roll. Another continuous structure would be longitudinal stripes that run in the circumferential direction around the entire pattern roll. An example of discontinuous pattern is horizontal, spaced-apart stripes that run in a direction that is, for example, perpendicular to the circumferential direction.

In some embodiments, the elements can have a largest dimension to smallest dimension ratio greater than 3, more preferably greater than 10 and still more preferably greater than 25. The largest dimension of the elements in one aspect is defined by the largest dimension of an article produced using the process described herein. Typically, this largest dimension can vary from about 0.1 mm to about 600 mm. These dimensions are defined by the dimensions of the distal surface of the raised surface elements. Preferably, the walls of the elements are tapered (i.e., narrower at the distal surface thereof than at the base). Such taper can ease cleaning of the pattern roll after extended run times. The walls can also be non tapered.

Exemplary processes by which the pattern roll can be provided with raised surface elements include: mechanical engraving (knurling), chemical etching, laser engraving and electromechanical engraving.

The height of the elements is not as critical as in gravure printing, since the material is deposited on the land areas thereof. Too high a height could result in difficult cleanup if the elastomer inadvertently ends up in the spaces between the raised surface elements on the pattern roll. The height of the elements above the ground surface of the pattern roll is suitably between 0.01 mm and 12 mm, preferably between 0.02 mm and 3.0 mm, and more preferably between 0.05 mm and 2.0 mm.

The elastomeric composition is preferably transferred to the pattern roll from an applicator roll in order to achieve even distribution across all of the raised elements and maintain process hygiene. Such indirect application to the raised pattern elements prevents buildup of elastomeric composition between the elements as would occur if the thermoplastic resin were applied directly onto the pattern roll by extrusion, spraying and similar direct application methods.

The elastomeric composition can be applied to the applicator roll by immersing the applicator roll in a bath of molten elastomer, slot coating, extrusion coating, spraying and other methods as are known to the art as suitable methods for providing an even coating of a material across the width of a roll.

If necessary the CD distribution of the elastomeric composition can be leveled by doctoring. As is known, a doctoring unit operation places an obstruction (e.g., a doctor blade) in direct contact with or at a fixed distance from a roll or other means of transporting the elastomeric composition to the pattern roll. The obstruction levels any unevenness in the CD distribution of the elastomer by causing portions to flow from high spots in the distribution to fill low spots. Typically, a doctor blade is a flexible steel blade. In this process, it may be preferable to heat the doctor blade, since the viscosity of the elastomer is high and also viscosity increases quickly if the elastomer is deposited on a surface having a temperature less than the elastomer application temperature. Doctoring also shears the elastomer. This could be a benefit for shear thinning materials, whose viscosity will decrease during doctoring, thus aiding the leveling process.

The land areas on the raised surface elements make a kiss contact with the elastomer layer on the applicator roll. It is important to accurately control: i) the coating thickness on the applicator roll and ii) the gap between the applicator and pattern rolls so as to control the amount of elastomeric composition that transfers. If the coating is too thin or the gap is too large, the pattern roll will not contact the elastomeric film and there will be no transfer. On the other hand, if the coating is too thick or the gap is too small, the elastomer will be forced in between the land areas in the pattern roll. This will result in a poor pattern definition for the transferred elastomeric composition and may require line shutdown for roll cleanup due to elastomer buildup between the raised surface elements.

After the elastomeric composition is delivered to the land area of the surface elements of the relatively cool pattern roll, it cools down prior to being transferred to the substrate. This cooling, and the resulting increase in viscosity, i.e., cohesive strength, is important to achieve adhesive failure at the point of transfer to the substrate. It is important to insure that at least a portion of the pattern roll surface has a surface temperature that is lower than the application temperature so as to provide this cooling. Such cooling is intended to reduce the temperature of the elastomeric composition to less than the order/disorder temperature thereof so as to increase the cohesive strength of the composition (The order/disorder temperature is the temperature where a block copolymer transitions from an ordered discernable phase into a single nondiscernable phase and is characterized by a substantial reduction in elastic modulus (G') as may determined via rheological measurements as a function of temperature). For typical elastomeric compositions used with the present invention the order/disorder temperature is at least about 140° C., sometimes 150° C. and even 180° C. or greater. As will be recognized, for high viscosity elastomeric compositions, cooling the deposited elastomer down by several tens of degrees Celsius may be sufficient to increase the cohesive strength to a point where the failure is adhesive and it is not necessary to cool the composition to the order/disorder temperature. Suitably, the surface temperature of the pattern roll is at least about 25° C. cooler than the temperature of the applicator roll. Preferably, the surface temperature is at least about 50° C. cooler, more preferably at least about 65° C. cooler. In order to maintain such reduced surface temperature, the pattern roll can be provided with a temperature control system as is known to the art in order to maintain the temperature of the pattern roll at a predetermined temperature that is less than the application temperature.

Optionally, in order to achieve good release of the elastomer from the raised surface elements, the roll could have a permanent or renewable release agent, e.g., a fluorochemical or silicone, on at least the land areas of the surface elements and preferably the entire exterior surface thereof. A renewable release agent can be added continuously in the process at a low add-on level. A suitable renewable release agent is described in copending U.S. patent application Ser. No. 10/151,562, filed on May 20, 2002. Permanent release coatings for process components are also known to the art and typically comprise fluoropolymers or silicone resins.

Many substrates are polyolefin based (polypropylene or polyethylene) and may be damaged (burnthrough or loss of loft due to calendaring) when elastomeric compositions are deposited on them. In the process described herein, however, the chances of damaging the substrate are reduced, since the pattern roll is relatively cool compared to the elastomer delivery temperature. In short, this process allows transfer of high viscosity elastomers to temperature-sensitive substrates, something that the conventional gravure printing process cannot do.

Using the process described herein, it is also possible to cool down the deposited elastomer substantially more, even to a temperature less than the glass transition temperature of one or more of the polymeric blocks comprising the elastomer, on the pattern roll such that the elastomer has sufficient mechanical strength to take on a solid, web-like form. In this form, it would now be possible to peel off the solidified elastomer from the pattern roll by applying some tension at the cool end. This solidified elastomer can, if desired, be stretched in the machine direction (e.g., by passing it through a nip between a downstream roll pair that is rotating at a higher speed than the pattern roll), bonded to the substrate, with an adhesive if necessary, and then allowed to retract to deliver live stretch. It is important to note that live stretch cannot be achieved by conventional printing processes, where a more fluid material comes in contact with the substrate.

As noted above, the elastomeric composition is delivered to the pattern roll from an applicator roll to insure even coating of the raised surface elements. The elastomeric composition is deposited onto the exterior surface of the applicator roll in a molten state from a delivery mechanism which may be selected from the group consisting of a slot coater, a bath, a sprayer, and an extruder. In both instances, however, the elastomeric composition is deposited on the applicator roll in a heated condition, cooled thereon and removed from the roll in a relatively cooler condition.

Without being bound by theory, in the case of letterpress application of elastomeric materials, oftentimes, when the failure is adhesive, the peel force needed to peel the elastomer from the pattern roll is much lower than when the failure is cohesive. See, Gent and Petrich, *Adhesion of Viscoelastic Materials to Rigid Substrates*, Proc. Roy. Soc. A, vol. 310, pp. 433-448 (1969). Also, when the failure is adhesive (also referred to as interfacial failure by Gent and Petrich), the peel force needed to peel off the elastomer from the pattern roll is almost changes little with increasing viscosity, which is quite beneficial especially in the case of high viscosity materials. In these instances, almost all of the elastomer is removed from the elements such that transfer is substantially complete. As used herein "substantially complete" or "substantially completely" means that no more than about 10%, preferably, no more than about 5%, and more preferably, no more than about 1%, of the elastomeric composition is left untransferred to the substrate from the letterpress application device, i.e., the roll. This substantially complete transfer is quite advantageous. For example, charring, which is a significant issue with unsaturated elastomers remaining in the dead zones inside gravure elements or pattern structures is minimized.

The Residual Elastomer test described in the TEST METHODS section below can be used to determine if the transfer is substantially complete. Residual Elastomer is defined as the weight of the elastomer remaining on the land areas of the pattern roll as a percent of the weight of the elastomer transferred to a length of the substrate equivalent to the pattern roll circumference. The Residual Elastomer value according to the method is suitably less than 10%, preferably less than 5%, and more preferably less than 1.

It is desirable to have the elastomeric composition at least partially penetrate the substrate at least in some locations, so that the resulting intermediate structure does not delaminate in subsequent processing or manufacturing steps or in the finished product. Preferably, the elastomeric composition penetrates only enough to provide the desired integrity during subsequent processing and use of the article. For example, if the substrate is a fibrous substrate, it is believed that it is only necessary for the elastomeric composition penetrate about one or two fiber diameters to provide such integrity. Additionally, such good bonding within the composite and/or its preform renders the use of adhesives optional. The degree of penetration may be affected by several factors: the viscosity of the elastomeric composition when in contact with the substrate, the porosity of the substrate, and the relative surface tension of the substrate and the elastomeric composition. The letterpress application process of the present invention allows partial cooling of the elastomeric composition before it contacts the substrate, and thus increases its viscosity and decreases the degree of penetration into the substrate. Alternatively, the elastomeric composition may be cooled by blowing chilled air/gas onto it prior to or while coming into contact with the substrate or the substrate may be cooled, e.g., by providing cooling to the backup roll. In another embodiment, the degree of penetration may be enhanced by passing the substrate/elastomeric composite between a pair of nip rolls so as to enhance penetration of the elastomeric composition into the substrate. The temperature of the nip rolls as well as the applied nip pressure provide further control of the degree of penetration.

In certain embodiments, it is possible to vary the amount of elastomeric composition deposited in different portions of the substrate, thereby varying the local stretch properties. For example, by changing the pattern on the pattern roll, the resulting elastomeric members can exhibit varying member densities (i.e., numbers of elastomeric members per unit area) from one area to another area of the composite. In one example of varied amount, a repeat unit on the pattern roll could correspond to a key dimension of a substrate (e.g., the length dimension of an absorbent article that would subsequently be made from the substrate) so as to provide different portions of the substrate with different amounts of elastomeric composition. Furthermore, two or more systems, with different patterns of raised surface elements or different elastomeric compositions applied to each, can also be used to deposit these elastomeric compositions in different portions of the substrate Furthermore, it is also possible to combine different deposition processes. For example, letterpress application can be combined with spraying or flexo printing, to obtain desired properties in the resulting stretch composites.

One embodiment of a process 100 of manufacturing a stretch composite is illustrated schematically in FIG. 1. This process may include a primary operation of making an intermediate structure, which includes the steps of supplying a first substrate; applying an elastomeric composition or material to the first substrate; and, optionally, joining with a second substrate. Process 100 may optionally include a secondary operation of incrementally stretching the elasticized substrate to provide additional extensibility to the substrate.

The primary operation of process 100 is shown in detail in FIG. 1. A substrate 34 is provided by a first supply roll 52 and moves in a machine direction through letterpress application system 105 which comprises an applicator roll 53, a pattern roll 54 and a back-up roll 56. Pattern roll 54 deposits an elastomeric composition that, after transfer to the substrate 34, forms elastomeric members thereon. The elastomeric composition is sufficiently soft at transfer to form an adequately strong bond between the elastomeric composition and the substrate to provide an elasticized substrate 35.

The elastomeric composition is delivered to pattern roll 54 from applicator roll 53. An elastomeric composition supply means 55 provides a metered amount of the elastomeric composition to applicator roll 53. Supply means 55 can include means 52 (e.g., a doctor blade) to level the elastomeric composition across the CD width of applicator roll 53. Optionally, a second doctor blade can be used to remove residual elastomeric composition from applicator roll 53 for recycle or disposal.

Figure 2:
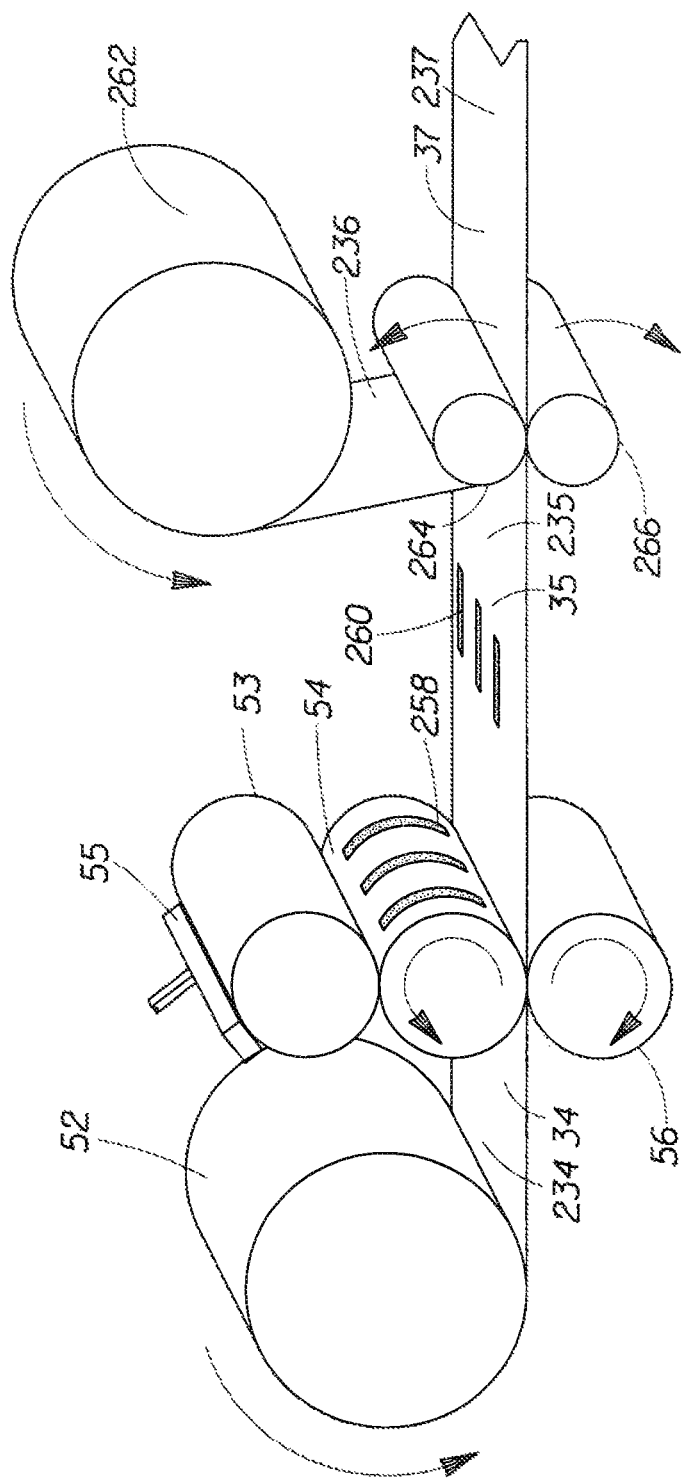
FIG. 2 is a perspective view of an apparatus for carrying out the process of the present invention.

As is shown in FIG. 2, the elastomeric composition is deposited on raised surface elements 258. After transfer, the elastomeric composition is deposited on substrate 234 as elastic members 260 to form elasticized substrate 235.

Optionally, an additional substrate 236 may be provided by a second supply roll 262 and combined with the elasticized substrate 235 via nip rolls 264, 266 to sandwich the elastomeric members 260 between substrates 234, 236 to form an intermediate structure 237. If necessary, adhesives may be used to bond the two substrates.

The elasticized substrate 235 and/or the intermediate structure 237 may be subjected to additional treatments such as cooling, pressing (e.g., passing between a pair of nip rolls), crosslinking, curing (e.g., via chemical, thermal, radiation methods), and combinations thereof, to enhance the elastic and mechanical properties of the elastomeric composition deposited thereon and of the resulting intermediate structure.

Figure 3:
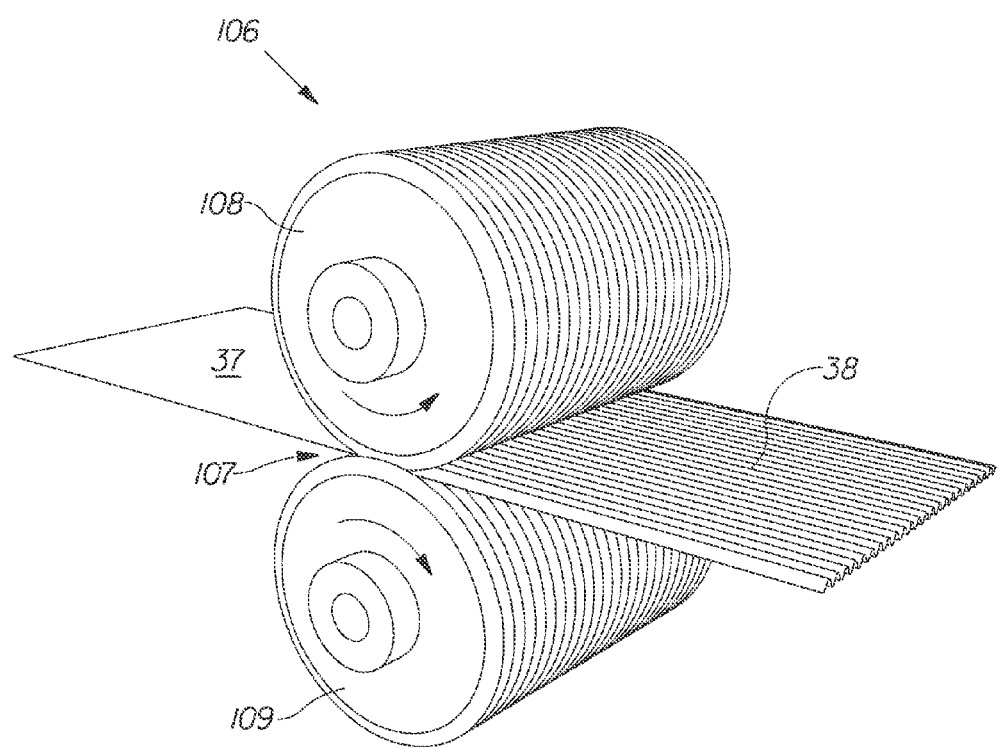
FIG. 3 is a perspective view of an apparatus for incrementally stretching an elasticized substrate produced according to the process of the present invention.

An exemplary secondary operation suitable for use in process 100 is shown as forming station 106 in FIG. 1 and in greater detail in FIG. 3. This secondary operation includes a forming station 106 which incrementally stretches the intermediate structure 37 (or the elasticized substrate 35) to the extent that the substrate is permanently elongated and intermediate structure 37 is converted into stretch composite 38. Due to this structural change, the substrate has a reduced resistance to stretch and the elastomeric members are able to stretch to the extent provided by the permanent elongation of the substrate.

The aforementioned process, known as "ring-rolling," to provide additional cross direction extensibility is shown in FIG. 3 where a pair of corrugated interengaging rolls 108, 109 are used to permanently elongate the substrate as it passes through nip 107 to reduce its resistance to stretch, may be a desirable incremental stretching operation of the present invention. Similarly, "gear rolling" can be used to provide incremental machine direction stretch. The resulting composite has a greater degree of stretchability in the portions that have been subjected to such additional process steps. Thus, such secondary operations provide additional flexibility in achieving stretch properties in localized portions of the stretch composite.

Methods for imparting stretchability to an extensible or otherwise substantially inelastic material by using corrugated interengaging rolls which incrementally stretch in the machine or cross-machine direction and permanently deform the material are disclosed in U.S. Pat. Nos. 4,116,892, 4,834, 741, 5,143,679, 5,156,793, 5,167,897, 5,422,172, and 5,518, 801. In some embodiments, the intermediate structure may be fed into the corrugated interengaging rolls at an angle with respect to the machine direction of this secondary operation. Alternatively, the secondary operation may employ a pair of interengaging grooved plates applied to the intermediate structure under pressure to achieve incremental stretching of the intermediate structure in localized portions.

Extensibility may also be imparted to the substrate via necking as described in U.S. Pat. Nos. 5,226,992 and 5,910, 224. In this process, the substrate is necked in one direction by applying tension, and the elastomer is printed while the substrate is still in the necked state. If necessary, this laminate can be incrementally stretched to further enhance the stretch properties. Another method of imparting extensibility is by consolidation as described in U.S. Pat. Nos. 5,914,084 and 6,114,263. As described, consolidation involves feeding a neckable nonwoven in a first direction, subjecting the nonwoven to incremental stretching in a direction perpendicular to the first, applying a tensioning force to the nonwoven to neck the nonwoven, subjecting the nonwoven to mechanical stabilization to provide a stabilized, extensible, necked nonwoven. Additionally, the requisite incremental stretching may be achieved by a combination of the stretching techniques detailed herein. As with necking, this laminate can optionally be incrementally stretched to further enhance stretch properties.

It is desirable that the extensible substrate does not exhibit meaningful resistance to stretch when the composite is subjected to a typical strain under in-use conditions. In-use strains experienced by the composite are due to the stretching when the article is applied to or removed from a wearer and when the article is being worn. The extensible substrate can be pre-strained to impart the desired stretchability to the composite. Typically, when the extensible substrate is pre-strained to about 1.5 times the maximum in-use strain (typically less than about 250% strain), the extensible substrate becomes permanently elongated such that it does not exhibit resistance to stretch within the range of in-use strain and the elastic properties of the composite are substantially provided only by the elastomeric members in the composite.

Suitable uses for the stretch composites that result from the processes of the present invention include disposable articles. Exemplary disposable articles include diapers, training pants, adult incontinence articles, sanitary napkins, garments like gloves, aprons, smocks, socks, etc. These disposable articles may comprise a stretch region that is selected from the group consisting of an ear, leg cuff, waist band, back panel, front panel, side panel, and combinations thereof, and these stretch regions comprise the stretch composites that are manufactured via the process of the present invention.

TEST METHODS

Peel Force

The peel force test measures the force required to peel an elastomeric composition in film form from a smooth stainless steel plate at room temperature.

Apparatus

Stainless Steel Plate: M$^c$ Master-Carr (Cleveland, Ohio), catalog number 8983K62, conforms to ASTM A240 The smooth stainless steel plate is made of 304 stainless steel and has a #2B finish; width=100 mm, length=75 mm, thickness=0.060

Silicone Rubber Sheet: M$^c$ Master-Carr #8979K111, high temperature silicone rubber, $\frac{1}{32}$" thick, 49 A Durometer Release Paper Paul N. Gardner Company, catalog #PC-RP-1K, 8.63"×11.25", ASTM D 4708/2370/1353

Hand Roller: A suitable roller can be fabricated as a 68 mm diameter steel roll having a 6 mm thick coating of hard rubber (65 Shore A) thereon. The finished roll has a weight of 2250 grams, a width of 6.35 cm.

Mylar Film: a 2 mils (0.05 mm) This Mylar film should be slightly wider and longer than the elastomer in order to ensure that it fully covers it.

Tensile Tester: A suitable instrument is available from MTS Systems Corp. of Cary, N.C. as model Alliance RT/1.

Sample Support: The support 400 used to hold the stainless steel plate during execution of this method is shown in FIG.

Figure 4A:
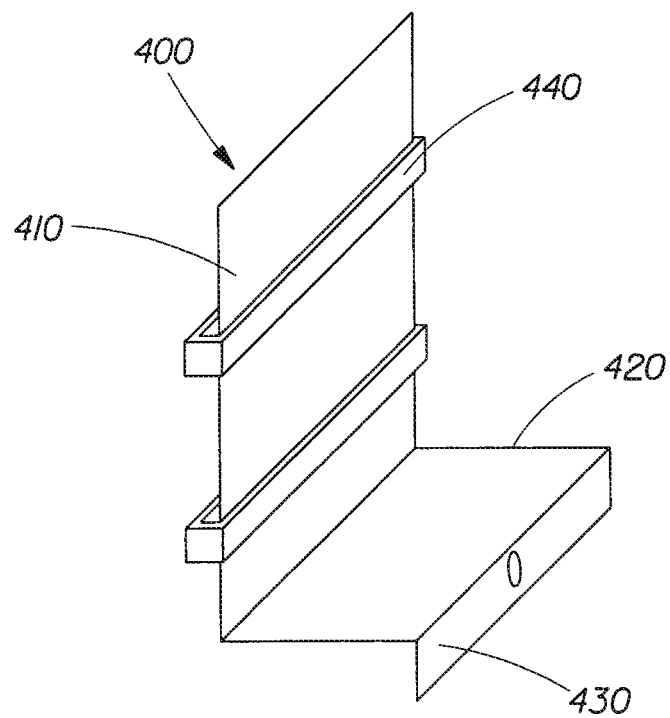
FIG. 4a is a perspective view of a sample holder used in the peel test.
Figure 4B:
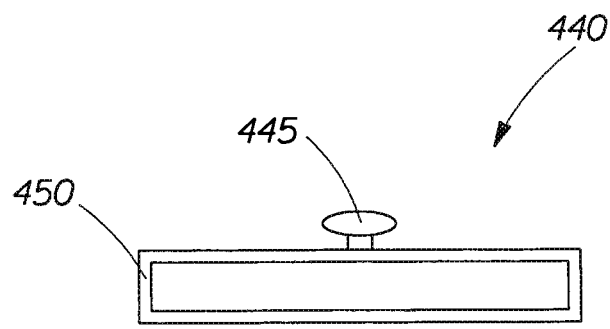
FIG. 4b is a perspective view of a clamp used in the peel test.

4a. It is a bent from a 120 mm×110 mm stainless steel plate so as to have the following dimensions:
Plate Width: 110 mm
First vertical portion 410-80 mm
Horizontal portion 420-25 mm
Second vertical portion 430-15 mm FIG. 4b shows one of a pair of clamps 440 used to insure that the stainless steel plate remains in stable contact with support 400 throughout the test. The clamps 440 may be conveniently made by bending 12 mm wide stainless steel into a rectangle 450 having a width of 111 mm (i.e., slightly wider than support 400)×5 mm deep. The clamps are also provided with a screw apparatus 445 for providing tension against the support 400.

Sample

Elastomeric Film: The film sample must have exactly the same composition as the elastomeric composition that is applied using the claimed process. Sample width is 2" (50.8 mm) wide by a minimum of 75 mm long by 14 mils±2 mils (0.356 mm±0.05 mm) thick The films are prepared by:
1) Weighing approximately 12 grams of the elastomeric composition of interest;
2) Compression molding the composition by placing the pre-weighed material between two pieces of 0.010 inch (0.03 mm) caliper PTFE (Teflon®) film;
3) Placing the film "sandwich" between preheated aluminum plates that are inserted into a Carver Press model 3853-0 with heated plates set to approximately 160° C.;
4) Heating the material for 3 minutes and then pressing it between the plates with an applied pressure of 2500 psi;
5) The formulation is allowed to flow under pressure for 30 seconds;
6) Quenching the resulting film to ambient temperature; and
7) Cutting the film into three equal portions.
8) Each portion is placed between films of PTFE and preheated aluminum plates and allowed to heat up to 160° C. for 1 minute in the Carver press before 2,000 psi of pressure is applied.
9) The formulation is allowed to flow under this pressure for 30 seconds.
10) The pressure is removed and the sample is rotated 90° and inserted back into the press and immediately 3,000 psi of pressure is applied.
11) The formulation is again allowed to flow for 30 seconds. The pressure is removed and the sample is flipped and inserted back into the press and immediately 4,000 psi of pressure is applied.
12) The formulation is again allowed to flow for 30 seconds.
13) The pressure is removed and the sample is rotated 90° and inserted back into the press and immediately 5,000 psi of pressure is applied.
14) The formulation is again allowed to flow for 30 seconds.
15) After the final pressing, the film is quenched to ambient temperature.
16) If necessary, two or more plies of material prepared according to steps 1-15 are laminated by layering the plies and repeating steps 8-15 to achieve a final sample thickness of 0.36±0.05 mm.
17) The films are cut into proper sample size according to the test methods described hereinabove.

Method
1) Place the smooth stainless steel plate (SS plate) on a metal support plate.
2) Place the silicone rubber sheet adjacent to the smooth SS plate. This silicone rubber sheet should have about the same thickness as the smooth SS plate.
3) Place the sample of the elastomeric film of interest on the smooth SS plate such that it is at least 50 mm on the smooth SS plate and at least 25 mm on the silicone rubber sheet.
4) Place the release paper on top of the elastomeric film and apply pressure with the hand roller. The hand roller is rolled over the test sample 10 times (1 time=1 forward and 1 return movement). The pressure applied is just the weight of the hand roller.
5) Remove the release paper and put the test sample on a SS support plate that is placed on a hot plate maintained at a temperature greater than the order/disorder temperature for the composition. It is necessary to heat the elastomer well above its order/disorder temperature in order to ensure that the elastomer is soft enough to bond with the smooth stainless steel plate. A temperature of 160 C should be sufficient for most compositions of interest.
6) Heat the test sample on the hot plate for 10 minutes±1 minute.
7) Remove the SS support plate along with the test sample and place it on a block of steel that is at room temperature.
8) Ten seconds after removal from the hot plate, place the Mylar film on the elastomer and apply pressure with the roller 10 times as before.
9) Allow the setup to cool down in air to room temperature.
10) Place the smooth SS plate, along with the elastomer and Mylar film, in the peel test grips on a tensile tester. The peel angle is 180 degrees and the measurements are made at room temperature.
11) Peel off the elastomer from the smooth SS plate at 10 inches/minute. The load increases first and then reaches a steady value.
12) Record this constant peel force and report it in gram force/cm width of the elastomer.
13) Repeat for a total of at least 3 replicates.
14) Report the average peel force and the standard deviation of the recorded measurements.

Residual Elastomer

This method is intended to measure the amount of residual elastomer on the pattern roll and uses this data to determine residual elastomer. In principle, a fluorescent material is incorporated into the elastomeric composition of interest and a curve relating amount of the composition to fluorescence is created. This curve is then used to relate measurements of fluorescence to the amount of thermoplastic elastomer remaining on the raised surface elements.

Materials

Fluorescer: A suitable fluorescent material is available from UV Process Supply Inc. of Chicago, Ill.

Apparatus

Any suitable apparatus capable of providing appropriate illumination and measuring the intensity of the emitted light may be used. The apparatus should be as compact as possible within the constraint of the measurement requirements.

Fluorimiter: Capable of receiving and measuring the intensity of emitted light from the fluorescent material. The fluorimeter should include an appropriate optical filter tuned to the characteristic wavelength of the light emitted by the fluorescer.

Exciter: Capable of providing light at the characteristic wavelength that is most efficient for energy transfer to the fluorescer. The exciter should include an optical filter to define the wavelength of the light used to illuminate the fluorescer.

Sample

Elastomer: Take a sample of elastomer that is at least three times the estimated volume of the elastomer supply apparatus on the application system being evaluated.

Determination of Fluorescer Concentration

1. Prepare a 0.01% solution of the elastomer in a suitable solvent.
2. Prepare a known concentration solution of the fluorescer in the same solvent.
3. To aliquots of the elastomer solution add aliquots of the fluorescer solution so as to provide mixed solutions that are equivalent to 0.01% solutions of elastomer that has had fluorescer at concentrations of 0.1%, 0.5%, 1%, 2% and 5% added thereto.
4. Calibrate the fluorimeter and exciter according to the manufacturer's instructions.
5. Determine the intensity of emitted light from each of the mixed solutions ($I_{0.1}$–$I_{0.8}$).
6. Choose a fluorescer concentration that provides an acceptable signal to noise ratio.

Preparation of Elastomer

The elastomer and the fluorescer are compounded so as to thoroughly disperse the fluorescer in the elastomer at the lowest concentration necessary to achieve an acceptable signal to noise ratio as determined from the intensity/concentration curve. GLS Corporation of M$^c$ Henry, Ill. is a suitable compounder for this operation.

Preparation of Standard Fluorescence Curve

1. Dissolve portions of the compounded elastomer using the fluorescer concentration as determined above in a suitable solvent at concentrations of 0.01%, 0.05%, 0.1%, 0.5% and 1%.
2. Measure and record the intensity of the fluorescence from each sample using the fluorimeter
3. Repeat steps 1 and 2 for two additional sets of samples.
4. Plot a curve of the concentration vs. the average intensity at each concentration.

Residual Elastomer Determination

1. Remove the noncompounded elastomer from the elastomer supply apparatus.
2. Fill the elastomer supply apparatus with the compounded elastomer.
3. Start up the letterpress application system.
4. Run the letterpress adhesive application system under production operating conditions until at least two supply system volumes of compounded elastomer have been consumed.

At the completion of steps 1-4 and before the remainder of the compounded elastomer is consumed conduct the following measurements while the system is running under production operating conditions.

5. Retract the applicator roll so as to prevent transfer of elastomer from the applicator roll to the pattern roll.
    6. Continue to run the process under production operating conditions with the applicator roll retracted for at least 20 revolutions of the pattern roll (approximately 10-30 seconds).
    7. Conduct a controlled line shutdown.
    8. Collect the product produced during the period in a manner that the sequence of products is maintained.
    9. Choose a pattern for further evaluation. As used herein a "pattern" is a portion of the elastomeric composition that has been deposited on the surface of the substrate from one or more raised pattern elements wherein the elements are located on a specific portion of the pattern roll.
    10. From the collected product, identify the first pattern produced where elastomer transferred thereto is visibly reduced. This pattern is indicative of the point in the process flow where the applicator roll was retracted.
    11. Collect 20 individual patterns that were produced after the first pattern with a visible reduction in transferred elastomer being careful to maintain the patterns in production order.
    12. Collect 20 individual products that were produced before the first pattern with a visible reduction in transferred elastomer being careful to maintain the products in production order.
    13. Number the samples 1 to 41 with sample number 1 being the that pattern that was produced with the greatest duration of time before the applicator roll was retracted and sample 41 being that pattern that was produced with the greatest duration of time after the applicator roll was retracted. As will be recognized, sample 21 is the sample visually identified in step 8.
    14. Extract, samples 1-25 using a suitable solvent.
    15. Measure the intensity of the fluorescence of the extracts of each sample. If necessary, the extracts can be concentrated using known methods to increase the measured intensity.
    16. Using samples 1-20, determine the process capability limits (mean intensity±3 standard deviations) of the application process for the pattern chosen.
    17. Compare the intensity of sample 21 to the process capability limits. If the intensity of sample 21 is within the process capability limits, proceed to step 16. If not, move backward through (i.e., toward sample 1) the samples to determine the first sample having an intensity within the process capability limits.
    18. For sample 21 (or alternative starting point as determined in step 15) and the next 5 samples in sequence determine the elastomer add-on (Add-On $Wt_{21}$–Add-On $Wt_{26}$) using the standard curve developed using the method described above.

$$19.\ \text{Percent Residual} = \frac{\sum_{22}^{26} \text{Add–}OnWt_i}{\sum_{21}^{26} \text{Add–}OnWt_i} \times 100$$

20. Repeat Steps 5-15 three more times.
21. Report average Percent Residual Elastomer, the individual calculated Percent Residual Elastomer values and all data used to calculate them.

Example 1

This example compares the properties of commercially available adhesives (elastomeric and nonelastomeric), a thermoplastic elastomer and exemplary non-adhesive elastomer compositions.

| Description | Peel Force (N/cm) | Type |
| --- | --- | --- |
| H2737[1] | 5.54 | Adhesive |
| H2031[2] | 14.40 | Adhesive |
| Vector 4211[3] | 2.31 | Non-adhesive |

-continued

| Description | Peel Force (N/cm) | Type |
|---|---|---|
| First non-adhesive elastomer[4] | 0.23 | Non-adhesive |
| Second non-adhesive elastomer[5] | 0.16 | Non-adhesive |

[1]Elastomeric adhesive from Bostik Findley of Wauwatosa, WI
[2]Adhesive from Bostik Findley
[3]Styrene/isoprene/styrene block copolymer available from Dexco Polymers LP, Houston, TX
[4]Vector 8508[a]                                                    20%
Low Molecular Weight Thermoplastic Elastomer[b]                      50%
Drakeol 600[c]                                                       25%
M Photoinitiator[d]                                                   5%
[a]Styrenic block copolymer from Dexco Company, Houston, TX
[b]Experimental Styrenic-isoprene-styrene block copolymer from Dexco
[c]Mineral oil from Pennzoil Co., Penrenco Div., Karns City, PA
[d]Experimental sample from National Starch and Chemicals Bridgewater, NJ
[5]Septon 4033[a]                                                    40%
SHF 401[b]                                                           40%
Dioctyldodecylterephthalate oligimer                                 20%
[a]Styrenic block copolymer from Kuraray America, Inc. of New York, NY
[b]Poly α olefin synthetic oil from ExxonMobile Chemical Co., Huston, TX.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of manufacturing a stretch composite, the process comprising the steps of:
    a) providing a polyolefin based substrate, wherein the substrate has a thickness between about 0.05 millimeters and about 2 millimeters;
    b) providing a letterpress adhesive application system comprising a pattern roll and an applicator roll;
    c) depositing a molten, non-adhesive, elastomeric composition onto the applicator roll;
    d) transferring only a portion of the elastomeric composition that is on the applicator roll, from the applicator roll to the pattern roll, by contacting the pattern roll with the elastomeric composition that is on the applicator roll; and
    e) transferring substantially all of the elastomeric composition from the pattern roll to the substrate, by contacting the substrate with the elastomeric composition that is on the pattern roll, without damaging the substrate.

2. The process of claim 1, wherein the providing of a polyolefin based substrate comprises providing a polypropylene based substrate.

3. The process of claim 1, wherein the providing of a polyolefin based substrate comprises providing a polyethylene based substrate.

4. The process of claim 1, wherein the providing of a polyolefin based substrate comprises providing a substrate, and wherein the substrate has a thickness between about 0.1 millimeters and about 1 millimeter.

5. The process of claim 1, wherein the providing of a polyolefin based substrate comprises providing a substrate, and wherein the substrate has a thickness between about 0.1 millimeters and about 0.5 millimeters.

6. The process of claim 1, wherein:
    the transferring of only a portion of the elastomeric composition takes place at a first temperature; and
    the transferring of substantially all of the elastomeric composition takes place at a second temperature that is less than the first temperature.

7. The process of claim 6, wherein the second temperature is at least about 25 degrees Celsius less than the first temperature.

8. The process of claim 6, wherein the second temperature is at least about 50 degrees Celsius less than the first temperature.

9. The process of claim 6, wherein the second temperature is at least about 65 degrees Celsius less than the first temperature.

10. The process of claim 6, wherein the second temperature is less than or equal to an order/disorder temperature of the elastomeric composition.

11. The process of claim 6, wherein the second temperature is less than or equal to an order/disorder temperature of the elastomeric composition, and wherein the order/disorder temperature is at least about 180 degrees Celsius.

12. The process of claim 6, wherein the second temperature is less than or equal to an order/disorder temperature of the elastomeric composition, and wherein the order/disorder temperature is at least about 150 degrees Celsius.

13. The process of claim 1, wherein the transferring of substantially all of the elastomeric composition comprises transferring at least about 90% of the elastomeric composition from the pattern roll to the substrate.

14. The process of claim 1, wherein the transferring of substantially all of the elastomeric composition comprises transferring at least about 95% of the elastomeric composition from the pattern roll to the substrate.

15. The process of claim 1, wherein the transferring of substantially all of the elastomeric composition comprises transferring at least about 99% of the elastomeric composition from the pattern roll to the substrate.

16. A process of manufacturing a stretch composite, the process comprising the steps of:
    a) providing a first substrate, the substrate moving in a machine direction, wherein the substrate has opposing first and second surfaces;
    b) providing a letterpress adhesive application system, the letterpress adhesive application system comprising a pattern roll and an applicator roll, each of the rolls having an exterior surface with a roll surface temperature, a portion of the exterior surface of the pattern roll comprising a predetermined pattern of raised surface elements;

c) depositing a molten, non-adhesive, elastomeric composition onto the exterior surface of the applicator roll, the composition having an application temperature, the application temperature being greater than the pattern roll surface temperature;

d) transferring a portion of the composition from the applicator roll to a distal surface of the raised elements so as to surface coat the raised elements, wherein the composition cohesively fails such that a portion of the composition also remains on the applicator roll; and e) cooling the transferred portion to a temperature between the application temperature and the pattern roll surface temperature causing a cohesive strength of the composition to increase such that the cohesive strength is greater than a peel force of the composition; and f) contacting the first surface of the substrate and the surface coated raised elements and substantially completely transferring the elastomeric composition from the distal surface of the raised surface elements to the first surface.

17. The process of claim 16, wherein the exterior surface of the pattern roll has a temperature that is at least 5° C. lower than at least one of the applicator roll surface temperature and the application temperature.

18. The process of claim 16, wherein the composition is deposited by a supply means selected from the group consisting of a slot coater, a bath, a sprayer, and an extruder.

19. The process of claim 16, wherein the elastomeric composition comprises thermoplastic elastomers and mineral oils and is substantially tackifier free.

20. The process of claim 16, wherein the at least a portion of the components of the elastomeric composition comprise crosslinkable materials.

21. The process of claim 16, wherein the elastomeric composition comprises from about 1 to about 70 wt% of a processing oil.

22. The process of claim 16, wherein the elastomeric composition comprises from about 1 to about 50 wt% of a non-elastomeric thermoplastic polymer.

23. The process of claim 16, wherein the substrate is stretched in the machine direction so as to neck the substrate in a cross machine direction prior to transfer of the composition.

24. The process of claim 16, wherein the substrate is incrementally stretched after the transfer of the composition so as permanently elongate at least a portion thereof.

25. The process of claim 16, wherein a second substrate is contacted with the elastomeric composition after the transfer of the composition.

26. A process of manufacturing a stretch composite, the process comprising the steps of:
 a) providing a polyolefin based substrate;
 b) providing a letterpress adhesive application system comprising a pattern roll and an applicator roll;
 c) depositing a molten, non-adhesive, elastomeric composition onto the applicator roll;
 d) transferring only a portion of the elastomeric composition that is on the applicator roll, from the applicator roll to the pattern roll, by contacting the pattern roll with the elastomeric composition that is on the applicator roll; and
 e) transferring at least 95% of the elastomeric composition from the pattern roll to the substrate, by contacting the substrate with the elastomeric composition that is on the pattern roll, without damaging the substrate.

\* \* \* \* \*